United States Patent
Fischer et al.

(10) Patent No.: US 7,309,859 B2
(45) Date of Patent: Dec. 18, 2007

(54) ION SAMPLING FOR APPI MASS SPECTROMETRY

(75) Inventors: Steven M. Fischer, Hayward, CA (US); Darrell L. Gourley, San Francisco, CA (US); Patricia H. Cormia, San Jose, CA (US); James L. Bertsch, Palo Alto, CA (US); Karl Hanold, Huntington Beach, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 190 days.

(21) Appl. No.: 11/290,187

(22) Filed: Nov. 30, 2005

(65) Prior Publication Data

US 2006/0076505 A1    Apr. 13, 2006

Related U.S. Application Data

(63) Continuation of application No. 10/863,967, filed on Jun. 8, 2004, now Pat. No. 7,002,146, which is a continuation of application No. 10/640,151, filed on Aug. 13, 2003, now Pat. No. 6,812,459, which is a continuation of application No. 10/155,364, filed on May 23, 2002, now Pat. No. 6,653,626, which is a continuation-in-part of application No. 09/910,222, filed on Jul. 19, 2001, now Pat. No. 6,498,343, which is a continuation of application No. 09/204,213, filed on Dec. 2, 1998, now Pat. No. 6,294,779, which is a continuation of application No. 09/030,676, filed on Feb. 25, 1998, now Pat. No. 6,278,110, which is a continuation of application No. 08/794,248, filed on Feb. 3, 1997, now Pat. No. 5,750,988, which is a continuation of application No. 08/555,250, filed on Nov. 8, 1995, now abandoned, which is a continuation-in-part of application No. 08/273,250, filed on Jul. 11, 1994, now Pat. No. 5,495,108.

(51) Int. Cl.
*H01J 49/26* (2006.01)

(52) U.S. Cl. .................................... 250/288

(58) Field of Classification Search ............ 250/288, 250/423 P, 425, 424, 423 R
See application file for complete search history.

(56) References Cited

U.S. PATENT DOCUMENTS 7,034,291 B1 * 4/2006 Fischer et al. ............ 250/288

* cited by examiner

*Primary Examiner*—Kiet T. Nguyen

(57) ABSTRACT

An atmospheric pressure ion source, e.g. for a mass spectrometer, that produces ions by atmospheric pressure photoionization (APPI). It includes a vaporizer, a photon source for photoionizing vapor molecules upon exit from the vaporizer, a passageway for transporting ions to, for example, a mass spectrometer system, and a means for directing the ions into the passageway. The center axis of the vaporizer and the center axis of the passageway form an angle that may be about 90 degrees. Included in the invention is a method for creating ions by atmospheric pressure photoionization along an axis and directing them into a passageway oriented at an angle to that axis.

10 Claims, 11 Drawing Sheets

ION SAMPLING FOR APPI MASS SPECTROMETRY

RELATED APPLICATIONS

This application is a continuation of U.S. patent application Ser. No. 10/863,967 filed Jun. 8, 2004 now U.S. Pat. No. 7,002,146 which is a continuation of U.S. patent application Ser. No. 10/640,151, filed Aug. 13, 2003 (now U.S. Pat. No. 6,812,459), which is in turn a continuation of U.S. patent application Ser. No. 10/155,364, filed May 23, 2002 (now U.S. Pat. No. 6,653,626), which is a continuation-in-part of U.S. patent application Ser. No. 09/910,222 filed Jul. 19, 2001 (now U.S. Pat. No. 6,498,343), which is a continuation of U.S. patent appliction Ser. No. 09/204,213 filed Dec. 2, 1998 (Now U.S. Pat. No. 6,294,779, issued Sep. 25, 2001), which is a continuation of U.S. patent application Ser. No. 09/030,676 filed Feb. 25, 1998 (now U.S. Pat. No. 6,278, 110, issued Aug. 21, 2001), which is a continuation of U.S. patent application Ser. No. 08/794,248 filed Feb. 3, 1997 (now U.S. Pat. No. 5,750,988, issued May 12, 1998), which is a continuation of U.S. patent application Ser. No. 08/555, 250, filed Nov. 8, 1995, now abandoned, which is a continuation-in-part of U.S. patent application Ser. No. 08/273, 250 filed Jul. 11, 1994 (now U.S. Pat. No. 5,495,108, issued Feb. 27, 1996).

FIELD OF THE INVENTION

The present invention relates to a method and apparatus for obtaining improved signal relative to noise without loss of ion collection efficiency for use in mass spectrometry, including liquid chromatography/mass spectrometry, especially as regards to the technique of generating analyte ions known as atmospheric pressure photoionization (APPI).

BACKGROUND INFORMATION

Liquid chromatography and mass spectrometry have proven powerful analytical tools in identifying molecular components of our world. Liquid is a fundamental separation technique. Mass spectrometry is a means of identifying "separated" components according to their characteristic "weight" or mass-to-charge ratio. The liquid effluent from liquid chromatography is prepared for ionization and analysis using any of a number of techniques. A conventional technique, atmospheric pressure ionization—electrospray (or simply "electrospray", for short), involves spraying the sample into fine droplets.

Early systems which employed electrospray liquid chromatography/mass spectrometry techniques utilized flow splitters that divided the high performance liquid chromatography column effluent. As a result of the effluent splitting, only a small portion, typically 5-50 micro liters per minute, was introduced into the "spray chamber". The bulk of the column effluent did not enter the spray chamber, but went directly to a waste or fraction collector. Because electrospray/mass spectrometry generally provides a concentration sensitive detector, it was not necessary to analyze the entire column effluent flow to obtain sensitive results. Results obtained by splitting are comparable in sensitivity to those obtained by introduction of the entire column effluent flow into the spray chamber (assuming equal charging and sampling efficiencies). Such low flow rates enabled generation of an electrosprayed aerosol solely through the manipulation of electrostatic forces. However, the use of flow splitters has performed poorly in that they experience plugging problems and poor reproducibility.

Newer electrospray systems generate a charged or ionized aerosol through the combination of electrostatic forces and some form of assisted nebulization. Nebulization is the process of breaking a steam of liquid into fine droplets. Nebulization may be "assisted" by a number of means, including but not limited to pneumatic, ultrasonic or thermal assists. The assisted nebulization generates an aerosol from the high performance liquid chromatography column effluent, while electric fields induce a charge on the aerosol droplets. The charged aerosol undergoes an ion evaporation process whereby desolvated analyte ions are produced. Ideally, only the desolvated ions enter the mass spectrometer for analysis.

It is a desired feature of an assisted nebulizer system that the vacuum system leading to the mass spectrometer permit desolvated ions to enter, but do not permit relatively large solvated droplets preset in the electrosprayed aerosol to enter. Several design approaches are currently in use, but none of the assisted nebulization methods currently practiced provide reliable sensitivity along with robust instrumentation.

In conventional electrospray/nebulization mass spectrometry systems, the electrosprayed aerosol exiting from the nebulizer is sprayed directly towards the sampling orifice or other entry into the vacuum system. That is, the electrosprayed aerosol exiting from the nebulizer and entry into the vacuum system are located along a common center axis, with the nebulizer effluent pointing directly at the entry into the vacuum system and with the nebulizer being considered to be located at an angle of zero (0) degrees relative to the common center axis.

One conventional approach directed at improving performance adjusts the aerosol to spray "off-axis". That is, the aerosol is sprayed "off-axis" at an angle of as much as 45 degrees with respect to the center axis of the sampling orifice. In addition, a counter current gas is passed around the sampling orifice to blow the solvated droplets away from the orifice. The gas velocities typically used generate a plume of small droplets. Optimal performance appears to be limited to a flow rate of 200 microliters per minute or lower.

In another system, an aerosol is generated pneumatically and aimed directly at the entrance of a heated capillary tube. The heated capillary exits into the vacuum system. Instead of desolvated ions entering the capillary, large charged droplets are drawn into the capillary and the droplets are desolvated while in transit. The evaporation process takes place in the capillary as well. Exiting the capillary in a supersonic jet of vapor, the analyte ions are subsequently focused, mass analysed and detected.

This system has several disadvantages and limitations, including sample degradation, re-clustering, and loss of sensitivity. Sensitive samples are degraded due to the heat. In the supersonic jet expansion exiting the capillary, the desolvated ions and vapor may recondense, resulting in solvent clusters and background signals. While these clusters may be re-dissociated by collisionally induced processes, this may interfere in identification of structural characteristics of the analyte samples. The large amount of solvent vapor, ions and droplets exiting the capillary require that the detector be arranged substantially off-axis with respect to the capillary to avoid noise due to neutral droplets string the detector. Removing the large volume of solvent entering the vacuum system requires higher capacity pumps.

Still another conventional system generates the electrosprayed aerosol ultrasonically, uses a counter current drying gas, and most typically operates with the electrosprayed aerosol directed at the sampling capillary. One disadvantage of this configuration is that optimal performance is effectively limited to less than five hundred (500) microliters per minute. Adequate handling of the aqueous mobile phase is problematic. Furthermore, the apparatus is complex and prone to mechanical and electronic failures.

In another conventional system, a pneumatic nebulizer is used at substantially higher inlet pressures (as compared with other systems). This results in a highly collimated and directed electrosprayed aerosol. This aerosol is aimed off axis to the side of the orifice and at the nozzle cap. Although this works competitively, there is still some noise which is probably due to stray droplets. The aerosol exiting the nebulizer has to be aimed carefully to minimize noise while maintaining signal intensity. Thus, repeated and tedious adjustments are often required.

In addition to atmospheric pressure ionization—electrospray, another conventional technique for preparing a liquid effluent for ionization and analysis is atmospheric pressure chemical ionization. Fundamentally, atmospheric pressure chemical ionization involves the conversion of the mobile phase and analyte from the liquid to the gas phase and then the ionization of the mobile phase and analyte molecules. Atmospheric pressure chemical ionization is a soft ionization technique that yields charged molecular ions and adduct ions. Atmospheric pressure chemical ionization actually includes several distinct ionization processes, with the relative influence of each process dependent on the chemistry of the mobile phase and the analyte.

Each of techniques of atmospheric pressure ionization—electrospray and atmospheric pressure chemical ionization is suited to different, and complementary, classes of molecular species. Briefly, atmospheric pressure ionization—electrospray is generally concentration dependent (that is to say, higher concentration equals better performance), and performs well in the analysis of moderately to highly polar molecules. It works well for large, biological molecules and pharmaceuticals, especially molecules that ionize in solution and exhibit multiple charging. Atmospheric pressure ionization—electrospray also performs well for small molecules, provided the molecule is fairly polar. Low flow rates enhance the performance of the atmospheric pressure ionization—electrospray technique. Atmospheric pressure chemical ionization, on the other hand, performs with less dependence on concentration and performs better on smaller nonpolar to moderately polar molecules. Higher flow rates enhance the performance of the atmospheric pressure chemical ionization technique. However, there are still analytes that do not ionize at all when these ionization techniques are employed, or which ionize weakly when these ionization techniques are employed.

In addition to the two conventionally employed ionization techniques of atmospheric pressure ionization—electrospray and atmospheric pressure chemical ionization, an alternative technique which has been developed for producing ions from a liquid sample is referred to as atmospheric pressure photoionization (APPI). Generally, the technique of atmospheric pressure photoionization provides a method of analyzing a sample of an analyte provided as a sample solution. According to one such technique, the sample solution is formed into an aerosol spray, for example in a nebulizer, and the solvent is evaporated. The sample stream is irradiated, e.g., subjected to photons, in a region at atmospheric pressure, in the vapor state after evaporation of the sprayed droplet. Collisions between the photons and the analyte result in ionization of the analyte. The analyte ions are passed from the atmospheric pressure ionization region into a mass analyzer for mass analysis.

According to another such technique, dopant is provided, either separately or as the solvent of the sample solution. The sample solution is formed into a spray, for example in a nebulizer, and the solvent is evaporated. The sample stream is irradiated, e.g., subjected to photons, in a region at atmospheric pressure to ionize the dopant. Again, this irradiation step takes place when the sample is in the vapor state after evaporation of the sprayed droplet. Then subsequent collisions between the ionized dopant and the analyte result in ionization of the analyte. Analyte ions are passed from the atmospheric pressure ionization region into a mass analyzer for mass analysis. This technique has been found to give enhanced ionization for some substances, as compared to atmospheric pressure chemical ionization.

Configurations for APPI in present use often provide unsatisfactory signal relative to noise and do not provide for optimal ion collection efficiency. Therefore, there exists a need for an improved method and apparatus for obtaining improved signal relative to noise without loss of ion collection efficiency for use in mass spectrometry, including liquid chromatography/mass spectrometry, especially as regards the technique of generating analyte ions known as atmospheric pressure photoionization.

SUMMARY OF THE INVENTION

The invention comprises an atmospheric pressure ion source, e.g. for a mass spectrometer, that produces ions by atmospheric pressure photoionization (APPI). It includes a vaporizer, a photon source for photoionizing vapor molecules upon exit from the vaporizer, a passageway for transporting ions to, for example, a mass spectrometer system, and a means for directing the ions into the passageway. In one embodiment, the passageway has a center axis situated substantially orthogonal to the center axis of the vaporizer. In another embodiment, the center axis of the passageway and the center axis of the vaporizer define an angle in the range of about 20 degrees to 180 degrees.

Included in the invention is a method for creating and transporting ions in an atmospheric pressure ion source by forming them with atmospheric pressure photoionization along an axis and directing them into a passageway oriented at an angle to that axis.

BRIEF DESCRIPTION OF THE DRAWINGS

FIG. 5 is a diagram that illustrates an apparatus for employing the atmospheric pressure chemical ionization technique, according to one embodiment of the present invention.

DETAILED DESCRIPTION OF THE INVENTION

Figure 1:
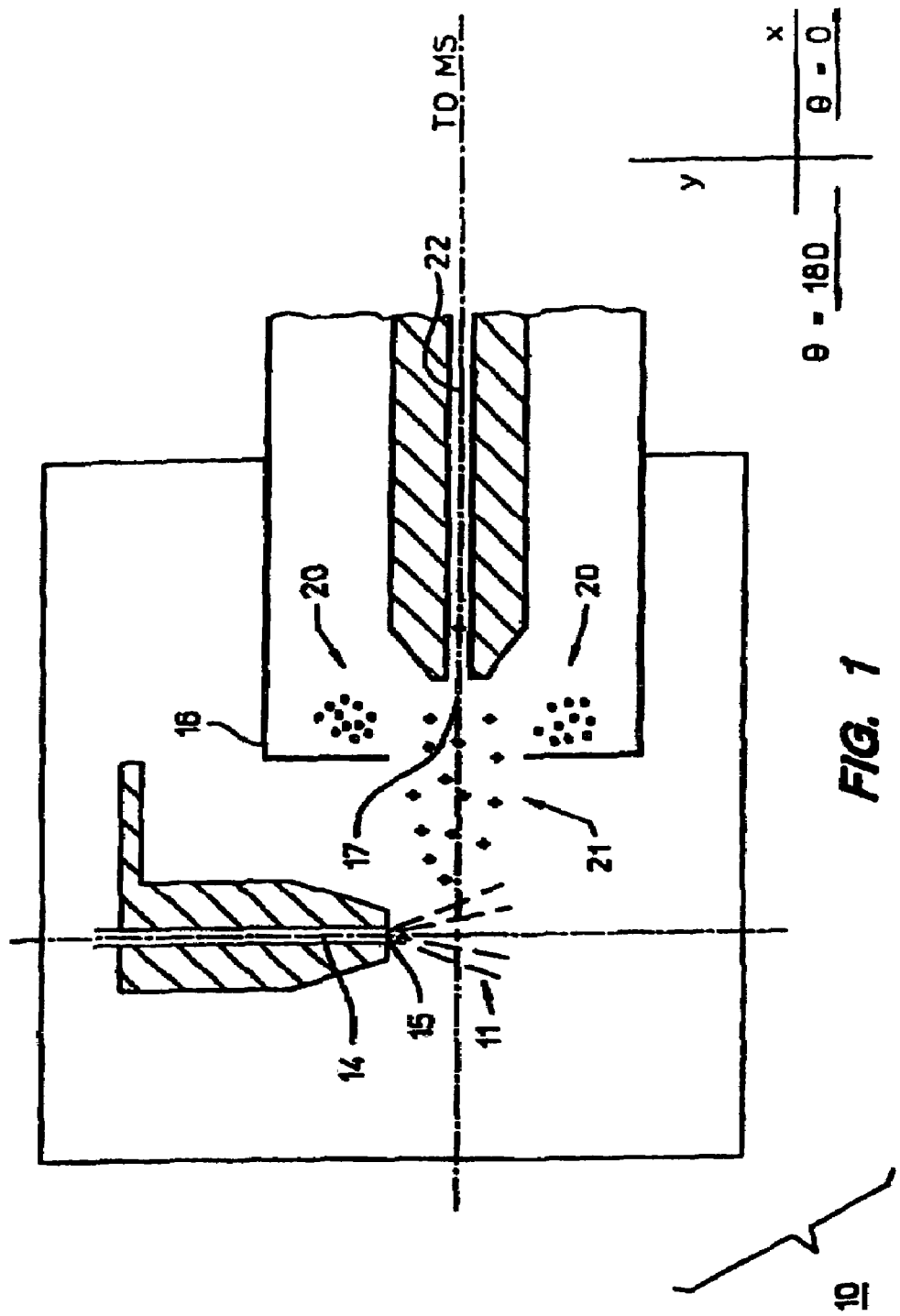
FIG. 1 is a diagram that illustrates an apparatus for employing the atmospheric pressure ionization—electrospray technique, according to one embodiment of the present invention.

FIG. 1 depicts an apparatus 10 configured according to one embodiment of the current invention. As in conventional sample introduction, a liquid sample is conducted through a nebulizer and into a first passageway 14, exiting via a second orifice 15 (the exit of the first passageway 14) under conditions which create a vapor of charged droplets or electrosprayed aerosol 11. This embodiment of the invention provides a rather different electrospray particle transport as compared with conventional electrospray processes. FIG. 1 depicts the transport of the electrospray droplets from the exit 15 of the first passageway 14, through the distance to the opening or orifice 17 of a second passageway 22, and entering the second passageway 22 where the orientation angle θ of the center axis of the exiting electrosprayed aerosol 11 and the center axis of the second passageway 22 is between 75 and 105 degrees with respect to each other. The angle may be greater than 105 with and, in principle, as great as 180 degrees; in practice, best results have been obtained at settings at or near 90 degrees. As shown in FIG. 1, the angle θ defines the location of the first passageway 14, that is, the nebulizer or other source of electrosprayed aerosol 11, relative to the second passageway 22, that is, the entry into the vacuum system. The angle θ is considered to be zero (0) degrees when the exit 15 for the electrosprayed aerosol 11 and the center axis of the first passageway 14 are pointing directly at the entrance 17 and the center axis of the second passageway 22. The angle θ is considered to be 180 degrees when the exit 15 for the electrosprayed aerosol 11 and the center axis of the first passageway 14 are pointing directly away from the entrance 17 and the center axis of the second passageway 22.

The charged droplets forming the electrosprayed aerosol are electrostatically attracted laterally across a gap between the exit 15 of the first passageway 14 into the opening 17 of the second passageway 22. The electrostatic attraction is generated by attaching voltage sources to components of the apparatus. A first voltage source (not shown) is connected to a housing 16 which houses the second passageway 22. The housing 16 is not necessarily an enclosure but may be any shape that can act as a guide for the ions and can support fluid dynamics of a drying gas (discussed below). A second voltage source (not shown) is connected to the second passageway 22. The first passageway 14 is generally kept at ground potential.

In the course of crossing the gap and approaching the opening 17 to the second passageway 22, especially after passing through an opening 21 in the housing 16 containing the second passageway 22, the electrosprayed aerosol is subjected to the cross flow of a gas 20—a condition that operates to remove solvent from the droplets, thereby leaving charged particles or ions. The ions are amenable to analysis by operation of an analytic instrument capable of detecting and measuring mass and charge of particles such as a mass spectrometer (not shown). The second passageway 22 exits into the mass spectrometer or equivalent instrument.

A standard electrospray mass spectrometry system with a pneumatic nebulizer provides the base structure. A spray box 12 (see FIG. 5) of plexiglass or some other suitable material for preventing shock and containing noxious vapors replaces the standard spray chamber. Within the spray box 12, the nebulizer and first passageway 14 may be arranged in a variety of configurations so long as the distances between the separate high voltage sources are sufficient to prevent discharges. Additional surfaces at high voltage may be used to shape the electrical fields experienced by the electrosprayed aerosol. In the embodiment depicted in FIG. 1, the system includes a drying gas 20 to aid desolvation and prevent droplets in the electrosprayed aerosol 11 from entering the orifice 17 of the second passageway 22 and the vacuum system (not shown). An alternate embodiment may include a heated capillary as the second passageway 22 in an internal source off-axis geometry, such that the capillary is off-axis with respect to quadrupole and detector components.

The positive ion configuration shown in FIG. 1 typically has the second voltage source set approximately at −4.5 kV, the first voltage source at −4 kV, and the first passageway 14 (wherein the passageway is comprised of a needle) set at relative ground. Gas, usually nitrogen at nominally 200 to 400 degrees Centigrade and approximately ten standard liters per minute, is typically used as a cross flow drying gas, although other gases can be used. The drying gas 20 flows across the aperture at approximately 90 degrees to the axis of the charged molecule in the electrosprayed aerosol.

The term "passageway", as used herein with respect to the second passageway, means "ion guide" in any form whatsoever. It is possible that the passageway is of such short length relative to the opening diameter that it may be called an orifice. Other ion guides, including capillaries, which are or may come to be used, can operate in the invention. The configuration herein are not meant to be restrictive, and those skilled in the art will see possible configurations not specifically mentioned here but which are included in the teaching and claims of this invention.

FIG. 5 illustrates the inventive apparatus as embodying and configured for atmospheric pressure chemical ionization. As can readily be observed by even a quick perusal of the FIG. 1 and FIG. 5 set side by side, the invention provides that embodiments for atmospheric pressure ionization—electrospray and atmospheric pressure chemical ionization—share much of the same hardware. It is apparent to one of average skill in the art that the configurations depicted herein, as well as many suggested by the illustrative examples, can be adopted interchangeably with relatively straightforward modification of input/output interfaces. FIG. 5 references elements common to FIG. 1 through use of the same numerical identification. By way of background, the conventional atmospheric pressure chemical ionization technique is a multistep process involving the steps of:

1) nebulization of the mobile phase and analyte (breaking into droplets);

2) vaporization of the droplets;

3) ionization of the mobile phase molecules by electrons from the charge source generating a corona discharge;

4) ionization of the analyte molecules by the mobile phase ions.

FIG. 5 depicts an apparatus 100 configured according to the current invention. The sample is nebulized (not shown) by any of number of known nebulization methods, and the resultant droplets proceed into and through a vaporizer 110. The vaporizer 110 is formed by a capillary or other tube-like structure 120 composed of glass or ceramic or other suitable material. The tube-like structure 120 is subjected to controlled heating through close association with a heating device 130. In both the tube-like structure 120 and the beating device 130 are of a length of several or more inches, the length being determined by the extent to which the heating device 130 is effectively insulated and, being insulated, how effectively the conditions in the vaporizer interior 135 promote ionization of the solvent molecules.

The vaporizer exit 140 allows the vaporized solvent and analyte in the aerosol to pass into an intervening space or gap 145. The molecules typically form a corona (not depicted) at this stage. Because the vaporizer is typically at ground potential, the exiting molecules "sees" a relatively large charge (either negative or positive) from a charge source 150. The charge source 150 is a charged point (a needle) in the preferred embodiment and the charge source is positioned so as to optimally induce charge transfer among the molecules collected in the gap 145. At this point, atmospheric pressure chemical ionization takes place. The charged point creates a corona discharge in the ambient nitrogen atmosphere. The hotjet of gas from exit (140), composed of solvent molecules and analyte molecules, enters the corona discharge region, wherein some of the molecules are ionized. Ionization processes include electron impact ionization and charge transfer reactions (also called chemical ionization). The ions are attracted toward the second passageway due to the electric fields created by the voltages applied to various components of the system. In the embodiment shown, the analyte ions are electrostatically attracted to a complementary (either positive or negative) charge from a voltage source (not shown) applied to the housing 16 of a second passageway 22 which leads to the mass analyzer (not shown) and a stronger relative charge from a voltage source (not shown) applied to the second passageway 22 itself, thereby attracting the analyte ions into the second passageway 22 through the opening 17 thereto.

The orientation angle θ defining the location of the vaporizer exit 140 relative to the second passageway 22 is between 75 and 105 degrees. The angle may be greater that 105 degrees; in principle, it may be as great as 180 degrees. However, best results have been obtained at angles at or near 90 degrees. As shown in FIG. 5, the angle θ, which defines the location of the vaporizer exit 140, is measured with respect to the center axis defined by the second passageway 22, that is, the entry into the vacuum system. The angle θ is considered to be zero (0) degrees when the vaporizer exit 140 and the center axis of the vaporizer 110 are pointing directly at the entrance 17 and the center axis of the second passageway 22. The angle θ is considered to be 180 degrees when the vaporizer exit 140 and the center axis of the vaporizer 110 are pointing directly away from the entrance 17 and the center axis of the second passageway 22. The vaporizer 110 is generally kept at ground potential.

In one embodiment the atmospheric pressure chemical ionization accessory accomplishes nebulization as mobile phase and analyte are sprayed out of a small needle. The concentric flow of nebulizing gas tears the stream of liquid into fine droplets in the aerosol. A heated tube in the atmospheric pressure chemical ionization accessory vaporizes the droplets of mobile phase and analyte as the droplets pass through the tube. The temperature of the tube is adjustable relative to the volatility of the mobile phase (low volatility indicates need for higher temperature). The selected temperature must substantially complete vaporization without thermally degrading the analyte.

After being vaporized, the mobile phase molecules ionize and subsequently react with and ionize the analyte molecules. The analyte ions thus produced are subject to the separation and direction afforded by the invention as taught herein.

EXAMPLES

Figure 2:
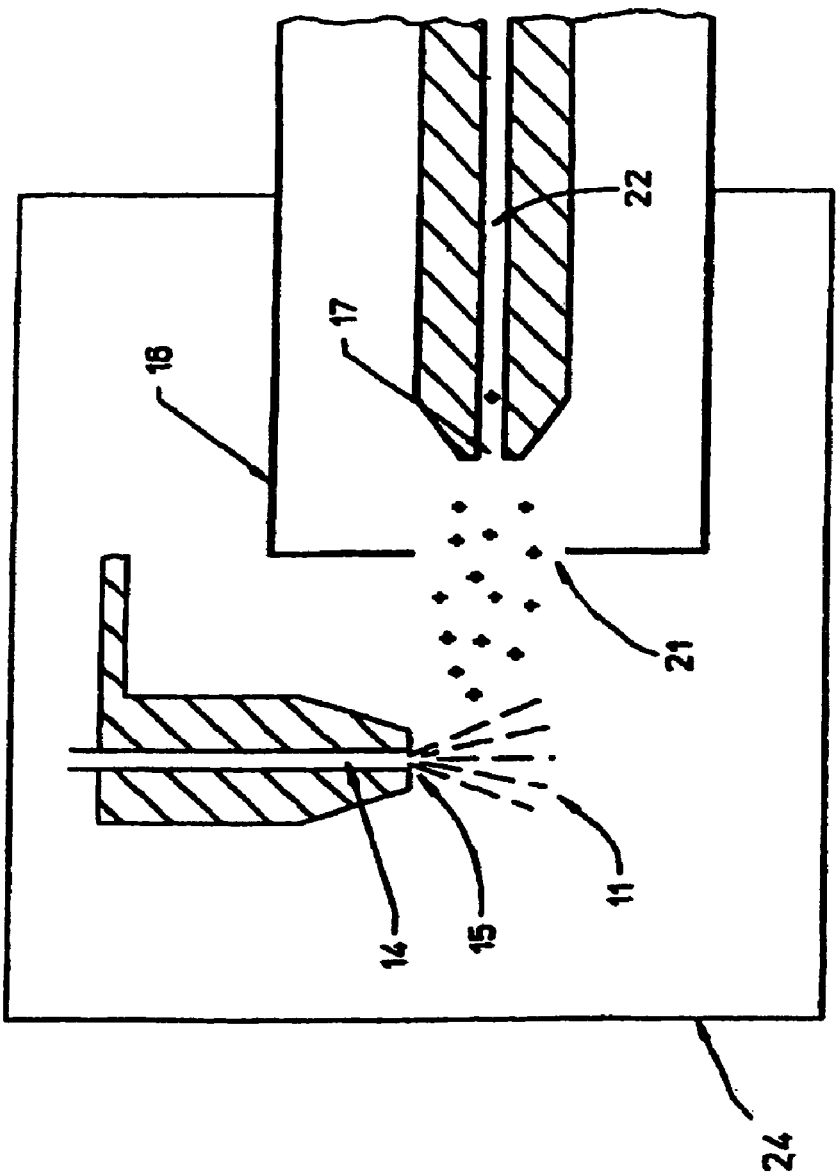
FIG. 2 is a diagram that illustrates an alternate embodiment of an apparatus for employing the atmospheric pressure ionization—electrospray technique, according to the present invention.

A number of different configurations have been proven possible. Examples of certain tested configurations follow:

FIG. 2 shows a configuration of the invention in which a third voltage source, a plate 24, is positioned beside the exit 15 of the first passageway 14 and distal to the side near to which the first voltage source, the opening 21 in the housing 16, and the opening 17 to the second passageway 22 are positioned. The plate 24 runs a positive voltage relative to the charge on the housing 16. Experiments show the electrosprayed aerosol "sees" a mean voltage between the plate 24 and the charged housing 16. Results suggest that the repeller effect may be captured and ion collection yield increased by careful sculpting of both the electric field and the gas flow patterns.

Figure 3:
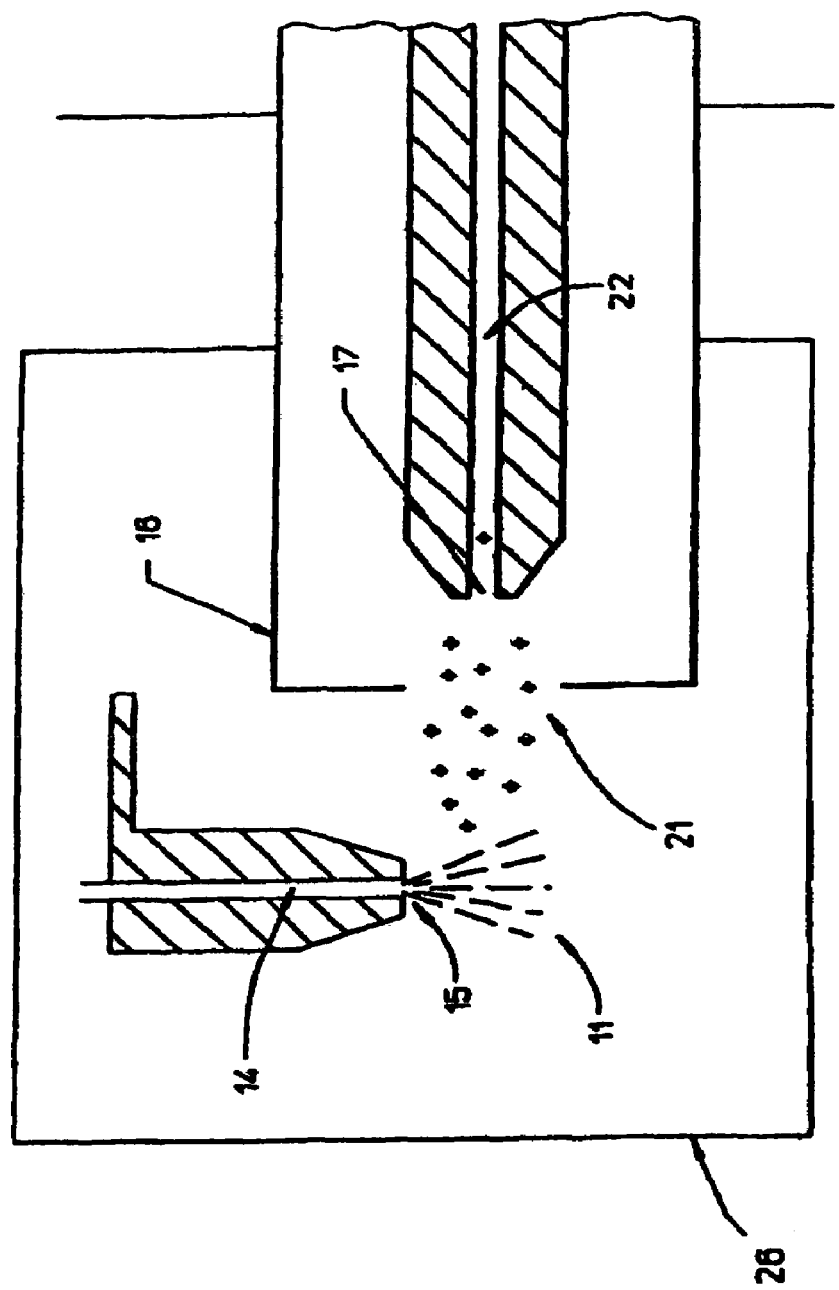
FIG. 3 is a diagram that illustrates an alternate embodiment of an apparatus for employing an atmospheric pressure ionization—electrospray apparatus, according to the present invention.

FIG. 3 shows a two-voltage source system as in FIG. 2 with the addition of a grounded spray chamber 26. The spray chamber 26 operates to contain the electrosprayed aerosol and route condensed vapor to waste.

Figure 4:
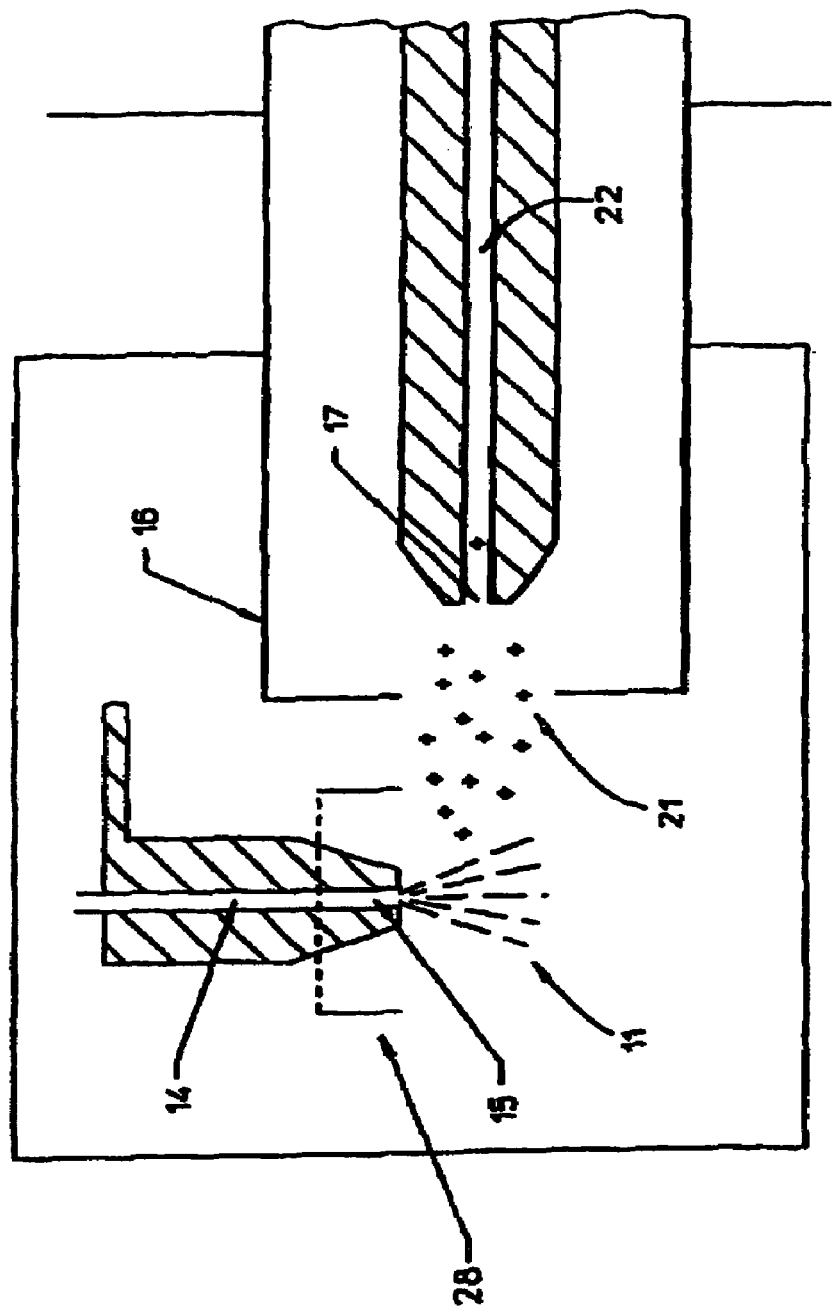
FIG. 4 is a diagram that illustrates an alternate embodiment of an apparatus for employing the atmospheric pressure ionization—electrospray technique, according to the present invention.

FIG. 4 shows the addition of a ring-shaped electrode 28 encircling the electrosprayed aerosol exiting from the needle or first passageway 14 at ground, with all of the elements configured as in FIG. 3. The ring-shaped electrode 28 induces a charge in the droplets by virtue of the potential difference in charge between the droplets and the ring-shaped electrode 28. Other potentials in the system can be used to direct the sampling of ions.

FIG. 5 illustrates an atmospheric pressure chemical ionization embodiment of the invention taught herein. The typical relative voltages are: source 150 set at between 1.2 kV and 2 kV; the surface of the housing 16 immediately adjacent to the entrance to the second passageway 22 set at approximately 3.5 kV; and the second passageway 22 set at a slightly greater charge of about 4 kV (both the surface of the housing 16 and the second passageway 22 oppositely charged from charge of the source 150). The delta voltage ranges from between about 4 to 6 kV.

Figure 6:
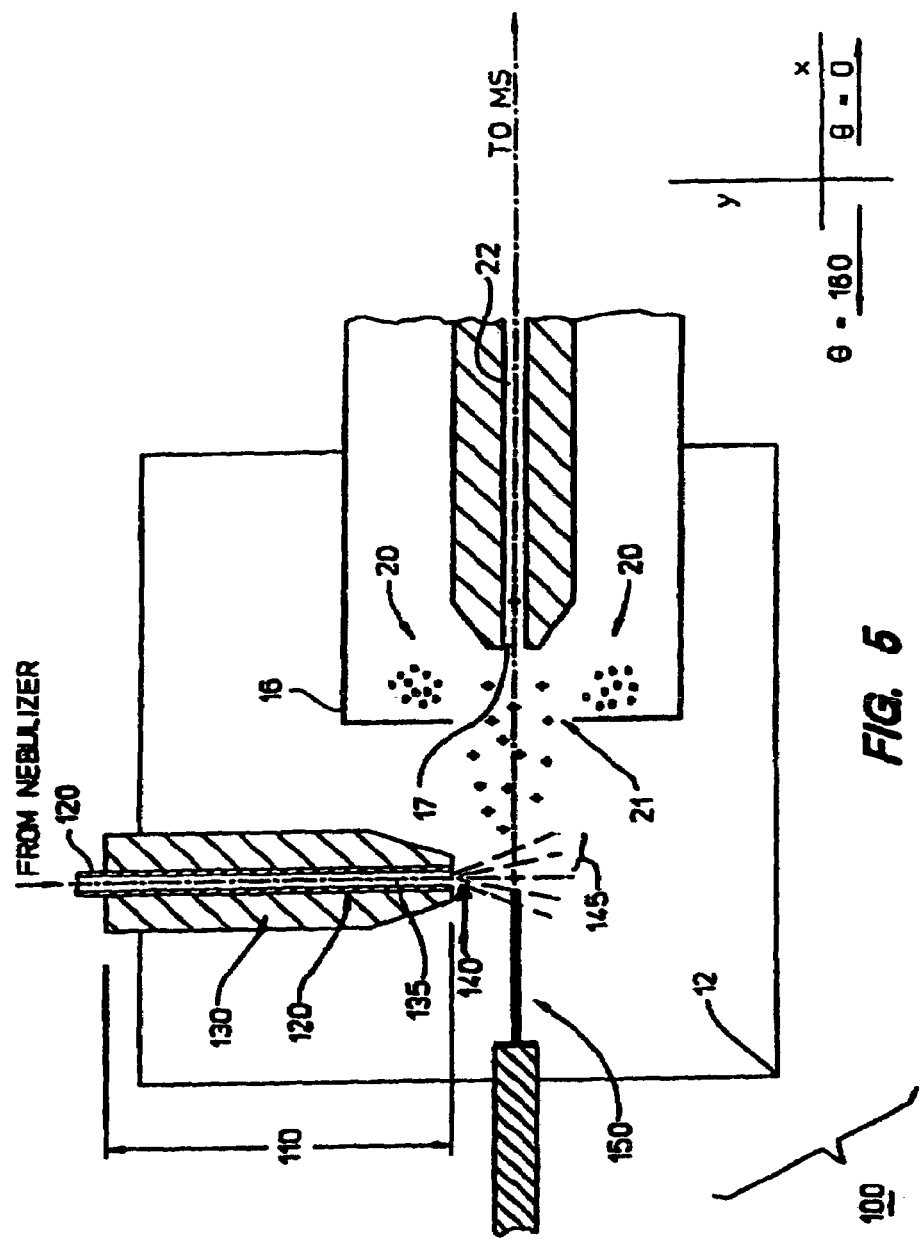
FIG. 6 is a diagram that illustrates an apparatus for employing the atmospheric pressure photoionization technique, according to one embodiment of the present invention.
Figure 6:
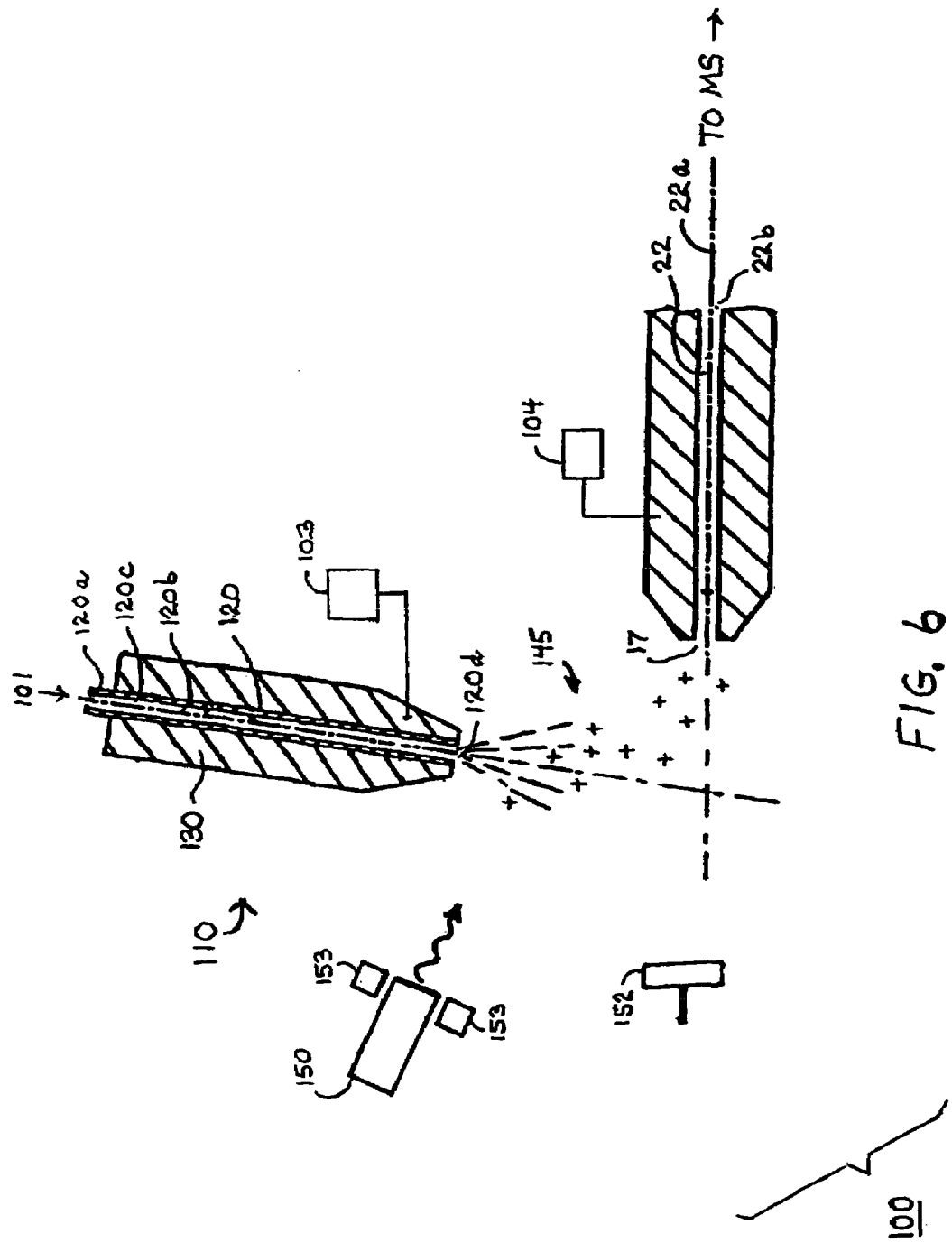

The present invention, according to another example embodiment thereof, relates to a method and apparatus for obtaining improved signal relative to noise without loss of ion collection efficiency for use in mass spectrometry, including liquid chromatography/mass spectrometry, as regards the technique of generating analyte ions known as atmospheric pressure photoionization. FIG. 6 illustrates an apparatus 100 configured according to one example embodiment of the present invention. A vaporizer 110 includes a first passageway 120, such as a capillary or other tube-like structure, composed of glass or ceramic or other suitable material. The first passageway 120 has an inlet orifice 120a, a center axis 120b, an interior vaporizer 120c through which a solute sample 101 may pass and in which the solute sample 101 is vaporized, and an exit orifice 120d.

According to one embodiment of the present invention, the fist passageway 120 is configured to be heated by a heating device 130 (details not shown). The length of both the first passageway 120 and the heating device 130 are determined by the extent to which the heating device 130 is effectively insulated and, being insulated, how effectively the conditions in the interior vaporization chamber 120c promote vaporization of the solvent molecules in the solute sample. Immediately after the exit orifice 120d of the first passageway 120 of the vaporizer 110, is an intervening space 145. Vaporized molecules of the solute sample 101 pass through the exit orifice 120d into the intervening space 145.

Although a center axis 120b has been described as related to the structure of the vaporizer and of the first passageway 120, it should be understood more broadly. Vaporized molecules of the solute sample 101 pass through the exit orifice 120d in a spray that is approximately centered on an axis herein called the molecular axis (not shown in FIG. 7). In FIG. 6, the molecular axis is approximately coincident with the center axis 120b of the vaporizer 120. It is possible to construct vaporizers for which the molecular axis is not coincident with a center axis of the vaporizer. In the invention, the direction of the spray of vaporized molecules is the direction that should be combined with other axes to form claimed angles. Thus, the term "center axis of the vaporizer" should be given the interpretation of the molecular axis when the molecular axis and what might be considered as a center axis of the vaporizer are not coincident.

Positioned adjacent to first passageway exit orifice 120d is a photon source 150, such as a ultraviolet (UV) lamp. According to one example embodiment of the present invention and as employed in the various example embodiments shown herein, the photon source ISO is a vacuum ultraviolet (VUV) lamp configured to generate ultraviolet radiation having a wavelength of less than 200 nm. The photon source 150 is configured to generate photons and direct them into the intervening space 145 at the molecules that pass through the exit orifice 120d of the vaporizer 110. It is intended that the wavelengths of the photons and the placement of the photon source be such as to photoionize vapor molecules that have passed through the exit orifice 120d into the intervening space 145. Advantageously, the photon wavelengths may be chosen to maximize production of analyte ions relative to ions of solvent molecules, but such a choice is not necessary to the invention. Also in some cases, the wavelengths can be chosen to maximize ionization of a dopant, which may be the solvent and which then ionizes the analyte.

Figure 9:
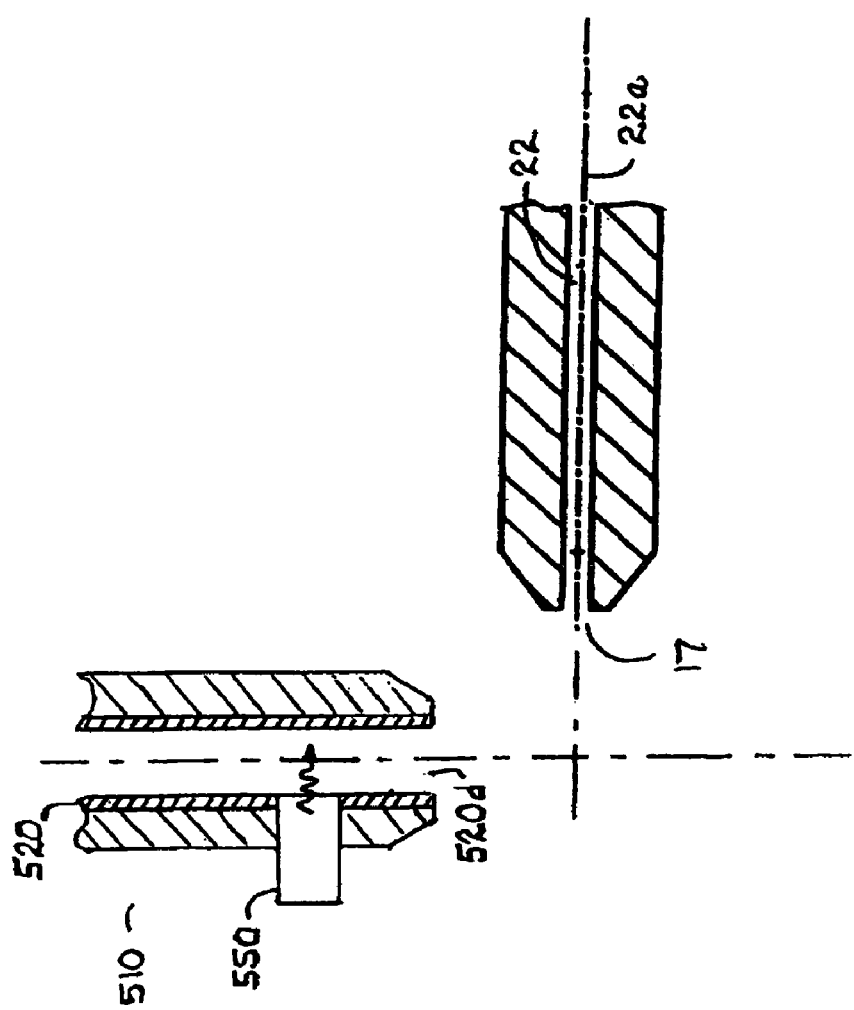
FIG. 9 is a diagram that illustrates a vaporizer for use in an apparatus for employing the atmospheric pressure photoionization technique, according to another embodiment of the present invention.
Figure 10:
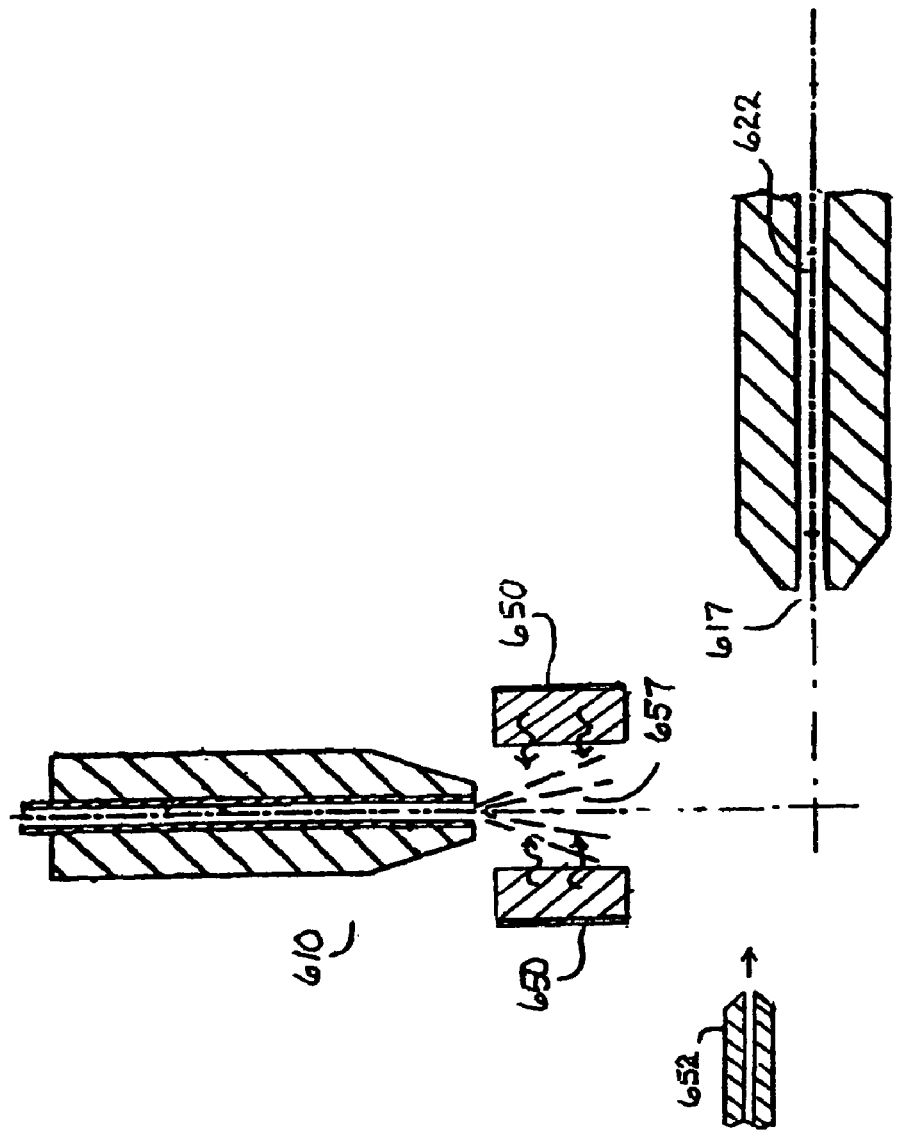
FIG. 10 is a diagram that illustrates an apparatus for employing the atmospheric pressure photoionization technique, according to still another embodiment of the present invention.

According to one example embodiment of the present invention, the photon source 150 is situated generally opposite to an inlet orifice 17 of a second passageway 22 (discussed in greater detail below), and pointing toward the intervening space 145. In accordance with alternate example embodiments, the photon source 150 is instead situated so as to be positioned to one side (e.g., not opposite) of the inlet orifice 17, or almost anywhere on a sphere surrounding inlet orifice 17 (with due regard for other structures such as the vaporizer 110, but so as to still finish photons that intersect the vaporized sample in the intervening space 145. Irrespective of the arrangement employed, it is preferred that the photon source 150 be placed relatively close to the ionization area to maximize the photon flux and ionization rate. FIG. 9 illustrates still another example embodiment of the present invention, whereby a photon source 550 is provided within a vaporizer 510 so as to cause ionization of the analyte molecules prior to the molecules exiting through the exit orifice 520d of the vaporizer 510. Yet another example embodiment is illustrated in FIG. 10, where the vapor stream from vaporizer 610 flows through the photon source 650 and analyte molecules are photoionized in a region 657 surrounded by that photon source.

As mentioned above, a second passageway 22 (see FIG. 6), such as a capillary tube, has an inlet orifice 17, a center axis 22a, and an exit 22b which may be, as mentioned previously, connected to or exit into a mass spectrometer. The center axis 120b of the first passageway 120 and the center axis 22a of the second passageway 22 define an angle therebetween that is in the range of about 20 degrees to 180 degrees. In one embodiment of the invention, e.g., as illustrated in FIG. 6, the angle is convenient at about 90 degrees or greater. The definitions of zero (0) and 180 degrees are as above.

One property of the angle between the center axis 120b and the center axis 22a, as contrasted with zero (0) angle, is that unevaporated material, e.g., solvent droplets, does not enter the second passageway 22. When used to furnish ions to a mass spectrometer, this property can result in less "noise" and thus higher sensitivity for detection of analyte samples.

Another property of the angle between the center axis 120b and the center axis 22a is the resulting flexibility in location of the photon source 150. The photon source 150 can be arranged to irradiate the vapor after it exits the vaporizer 110 and thus where the vaporization is more complete than within the vaporizer itself. Many such arrangements of the photon source 150 are now possible. The result can be a larger number of analyte ions produced, again leading to higher sensitivity for detection of analyte samples when the ion source is used with a mass spectrometer.

In the present invention, the lower limit of the angle defined by the center axis 120b of the vaporizer and the center axis 22a of the second passageway is about 20 degrees and is determined by the consideration that two advantages of the configuration of the invention begin to disappear at small angles. Thus, as the angle decreases, more solvent droplets enter the second passageway 22 and also it becomes more difficult to place the photon source 150 advantageously. Angles greater than 60 degrees are generally more satisfactory than smaller angles, and performance often is better yet with angles of about 90 degrees or greater.

The configuration and arrangement of the vaporizer and the second passageway can be such that the center axis 120b of the vaporizer and the center axis 22a of the second passageway do not intersect, that is, the two axes may not lie in the same plane. In those cases, the angle may be defined geometrically by drawing a line connecting the two axes such that the line is orthogonal to each, then displacing one axis parallel to itself along that line until the other axis is intersected. The angle is then defined as described above.

As previously mentioned, the term "passageway", as used herein means "ion guide" in any form whatsoever. The term should be considered to include any physical structure required for creating a passage for the transport of ions. It is possible that the second passageway 22 is of such short length relative to the opening diameter of the inlet orifice 17 that the second passageway 22 may be called an orifice. In that case, center axis 22a may be along the direction of the normal to the plane of the orifice. Other "ion guides" which are, or may come to be, used can operate in the invention. The use of the term "passageway" is not intended to limit the scope of the present invention.

FIG. 6 also illustrates a means for generating an electric field. The electric field means is employed to direct the ionized molecules from the intervening space 145 into the inlet orifice 17 of the second passageway 22. It is noted that one advantage of using the atmospheric pressure photoionization technique is that, unlike the electrospray ionization and atmospheric pressure chemical ionization techniques, it does not employ an electric field in the ion production process. Electrospray ionization and atmospheric pressure chemical ionization techniques use electric fields to help generate ions. As a result, the feasible voltage and electrode configurations employed by these techniques are limited by the requirement that electric fields must be of appropriate magnitudes and shapes for use in the ion production. By contrast, the voltage and electrode configurations in the atmospheric pressure photoionization technique are not required to produce electric fields for the ionization process. Instead, the atmospheric pressure photoionization technique of the present invention advantageously employs an electric field means to merely move the ions created by the photons to the desired location, e.g., to the inlet orifice 17 of the second passageway 22. The electric field means does not have the additional requirement of having to assist in ionization of the analyte sample In the atmospheric pressure photoionization technique of the present invention, there are various conceivable configurations by which an electric field may be established in order that ions are directed towards the inlet orifice 17 of the second passageway 22 and into a mass spectrometer. In the embodiment illustrated in FIG. 6, the electric field means includes a first voltage source 103 and a second voltage source 104 that are coupled to electrodes to generate an electric field. The first voltage source 103 is coupled to the first passageway 120 of the vaporizer 110 and the second voltage source 104 is coupled to the second passageway 22, such that an electric field is established between the exit orifice 120d of the first passageway 120 and the inlet orifice 17 of the second passageway 22. The shape of the electric field so established is determined by the exact configurations and placements of the electrodes (e.g., the first passageway and the second passageway) and their surroundings. The shape and magnitude of the electric field generated by the voltage sources 103 and 104 are such as to cause the field to move and direct the ionized molecules from the intervening space 145 into the inlet orifice 17 of the second passageway 22.

The term "voltage source" should be interpreted broadly. A voltage source, for example, need not be an actual electrical power supply. It might, for example, be simply a connection to ground, establishing a ground potential (commonly called zero voltage), or to another conductor at a definite potential. An electric field is created by a potential difference between conductors or electrodes. For a given potential difference or set of potential differences, the field is the same regardless of the absolute potentials. A "voltage source", as the term is used herein, is anything that establishes the potential on whatever it is connected to. In the example embodiment of FIG. 6, the first passageway 120 can be at or about ground potential (within about 300 V of zero) and the second passageway 22 can be at a high negative potential, or the fist passageway 120 can be at high positive potential and the second passageway 22 at or about ground. (The polarities given are for positive ions.) All conductors and electrodes in the ion source are connected to voltage sources so that they have established potentials. Although operation of the ion source with one or more "floating" electrodes is possible, it is usually not preferred.

Of course, the means for generating an electric field is not limited to a pair of voltage sources coupled to respective passageways. For instance, according to an example embodiment (and as illustrated as an optional feature in FIG. 6), an auxiliary electrode 152 connected to a voltage source (not shown) is provided that establishes an electric field between it and the second passageway 22 to assist motion of ions into the latter. According to another example embodiment (and as illustrated as an optional feature in FIG. 6), a lamp electrode 153 connected to a voltage source (not shown) is provided and is positioned so as to surround the photon source 150, thereby establishing an electric field between the inlet orifice 17 of the second passageway 22 and the lamp electrode 153. According to another example embodiment, the vaporizer 110 may be employed as an electrode. According to still another embodiment and as illustrated in FIG. 9, a photon source 550 is positioned in a vaporizer 510 such that ions are formed internal to the vaporizer 510, and the exit orifice 520d of the vaporizer 510 is employed as an electrode to establish an electric field relative to the inlet orifice of a second passageway. Furthermore, it is noted that while embodiments have been described herein having two electrodes coupled to respective voltage sources, alternative embodiments of the present invention may employ one or more electrodes coupled to a voltage source, and one or more electrodes coupled to or maintained substantially at ground, e.g., at ground or near ground. Alternatively, the electric field means may include a single voltage source having a resistive divider, or any other conceivable arrangement that is capable of generating an electric field for directing ionized molecules from the intervening space 145 into the inlet orifice 17 of the second passageway 22.

As mentioned above, according to a preferred embodiment, the atmospheric pressure photoionization technique employs as the electric field means an electrode plate around the photon lamp (also referred to as a "lamp electrode") to establish the electric field relative to the inlet orifice 17 of the second passageway 22. An example of such a lamp electrode is illustrated as lamp electrode 153 in FIG. 6. Preferably, according to this embodiment, the second passageway 22 is maintained at a high voltage (e.g., −1500 to −6000 Volts for the positive ion and +1500 to +6000 Volts for the negative ion), while the vaporizer 110 and the lamp electrode 153 are coupled to ground. However, it is recognized that, in accordance with other example embodiments, this arrangement could be reversed such that the potential of the second passageway is near or at ground while the vaporizer and the lamp electrode are maintained at the specified, or other predetermined, voltages.

In operation, according to the example embodiment of the present invention illustrated in FIG. 6, a liquid solute sample 101, which is comprised of a solvent and an analyte and which may be in the form of an aerosol, proceeds through the first passageway 120 of the vaporizer 110. The aerosol within the first passageway 120 is heated by the heating device 130 in order to promote vaporization of the aerosol. The vaporized molecules exit the first passageway 120 of the vaporizer 110 through the first passageway exit 120d and into the intervening space 145. The vapor molecules exiting from first passageway exit 120d are subjected to photons generated by the photon source 150. The interaction of the photons from the photon source 150 with the vapor molecules causes ionization of the analyte. Once formed, the analyte ions are moved and directed by the electric field generated by the electric field means into the second passageway 22 through the opening 17. The analyte ions pass through the second passageway 22 into a mass analyzer (not shown), such as a mass spectrometer, in order to be analyzed.

Figure 7:
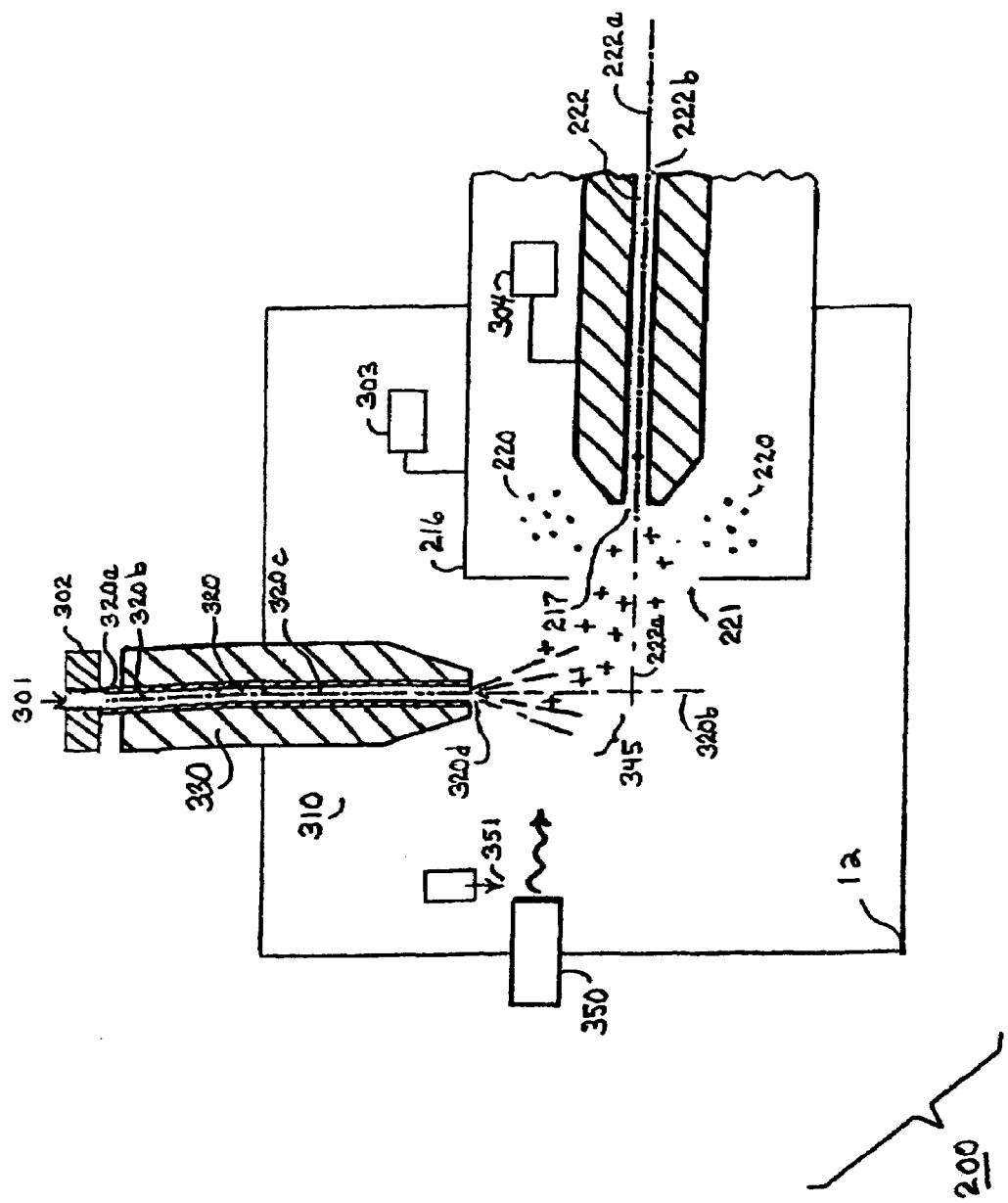
FIG. 7 is a diagram that illustrates an apparatus for employing the atmospheric pressure photoionization technique, according to another embodiment of the present invention

FIG. 7 illustrates an apparatus 200 configured according to another example embodiment of the present invention. In this embodiment, a nebulizer 302 is configured to receive via its inlet a solute sample 301. The nebulizer 302 is coupled to a vaporizer 310. The vaporizer 310 includes a first passageway 320 that has an inlet orifice 320a, a center axis 320b, an interior vaporization chamber 320c and an exit orifice 320d. The first passageway 320 is configured to be heated by a heating device 330 to promote vaporization of the solvent molecules. At the end of the first passageway 320 of the vaporizer 310 is an intervening space 345.

Positioned adjacent to first passageway exit 320d is a photon source 350, such as a UV lamp. As discussed above, according to one example embodiment of the present invention, the photon source 350 may be a vacuum UV lamp configured to generate ultraviolet radiation having a wavelength of less than 200 nm, and is configured to generate and direct photons into the intervening space 345 at the molecules that pass through the exit orifice 320d of the vaporizer 310. As previously discussed, the photon source 350 may be situated generally opposite to an inlet orifice 217 of a second passageway 222, positioned to one side (e.g., not opposite) of the inlet orifice 217, or located almost anywhere on a sphere surrounding inlet orifice 217 (with due regard for other structures such as the vaporizer 310, but so as to still furnish photons that intersect the vaporized sample in the intervening space 345. Preferably, the photon source 350 is situated such that the photons intersect the vaporized sample in the intervening space 345 approximately in front of the inlet orifice 217 of second passageway 222, and is placed relatively close to the ionization area to maximize the photon flux and ionization rate.

According to the example embodiment illustrated in FIG. 7, a drying gas source (not shown) provides a stream of drying gas 351 across photon source 350 in order to prevent build-up on photon source 350. This build-up may result from exposure to contaminants such as the solvent, buffers, sample, etc. This contamination can over time build up on the lens, causing a loss in UV transmission and a decline in ionization efficiency. It may also lead to noise or spurious background. One type of gas that may be employed is dry nitrogen, although other gases may also be employed. Advantageously, the gas that is employed as the photon source drying gas stream 351 is the same as the gas employed as the nebulizer gas, thereby eliminating the requirement to employ more than one kind of gas in the apparatus. In addition, the stream of drying gas 351 may be maintained at a relatively high temperature, up to about 300° C., more usually about 100° C., in order to more effectively reduce the likelihood of condensation on the lamp.

In the embodiment shown in FIG. 7, an electrically conductive housing 216 having a housing opening 221 is positioned such that housing opening 221 is adjacent to the first passageway exit 320d of first passageway 320. A second passageway 222, such as a capillary tube of a mass spectrometer, is arranged within the housing 216 adjacent to the housing opening 221. The second passageway 222 has an inlet orifice 217, a center axis 222a, and an exit orifice 222b which may be, as mentioned previously, connected to or exit into a mass spectrometer. As previously mentioned, the term "passageway", as used herein means "ion guide" in any form whatsoever. The center axis 320b of the first passageway 320 can be substantially orthogonal relative to the center axis 222a of the second passageway 222. More generally, the center axis 320b of the first passageway 320 and the center axis 222a of the second passageway 222 define an angle therebetween that is in the range of about 20 degrees to 180 degrees.

FIG. 7 also illustrates a means for generating an electric field that is employed to direct the ionized molecules from the intervening space 345 into the inlet orifice 217 of the second passageway 222. As previously discussed in connection with FIG. 6, there are many possible configurations by which an electric field may be established, e.g., generated and shaped, in order that ionized molecules are directed towards the inlet orifice 217 of the second passageway 222. In the embodiment illustrated in FIG. 7, the electric field means includes a fist voltage source 303 and a second voltage source 304. The first voltage source 303 is coupled to the housing 216 and the second voltage supply source 304 is coupled to the second passageway 222, such that a field is generated to direct the ionized molecules from the intervening space 345 into the inlet orifice 217 of the second passageway 222. Again, as previously discussed, the means for generating the electric field is not limited to a pair of voltage sources coupled to respective electrodes, but may include any conceivable arrangement that is capable of generating an electric field for directing ionized molecules from the intervening space 345 into the inlet orifice 217 of the second passageway 222, e.g., electrodes in various configurations coupled to one or more voltage sources or coupled to or maintained substantially at ground, e.g., at ground or near ground. In still another example embodiment, an additional electrode, which may be the housing 216, is positioned between the inlet orifice of the second passageway and the other electrodes. Advantageously, this additional electrode has a voltage that differs from the voltage of the second passageway by about 500 volts. The positioning of this additional electrode between the inlet orifice of the second passageway and the other electrodes permits a small amount of heated drying gas 220 to be directed in front of the inlet orifice of the second passageway. The use of this heated drying gas in this embodiment helps to reduce the amount of noise experienced by the system without affecting the signal.

Figure 8:
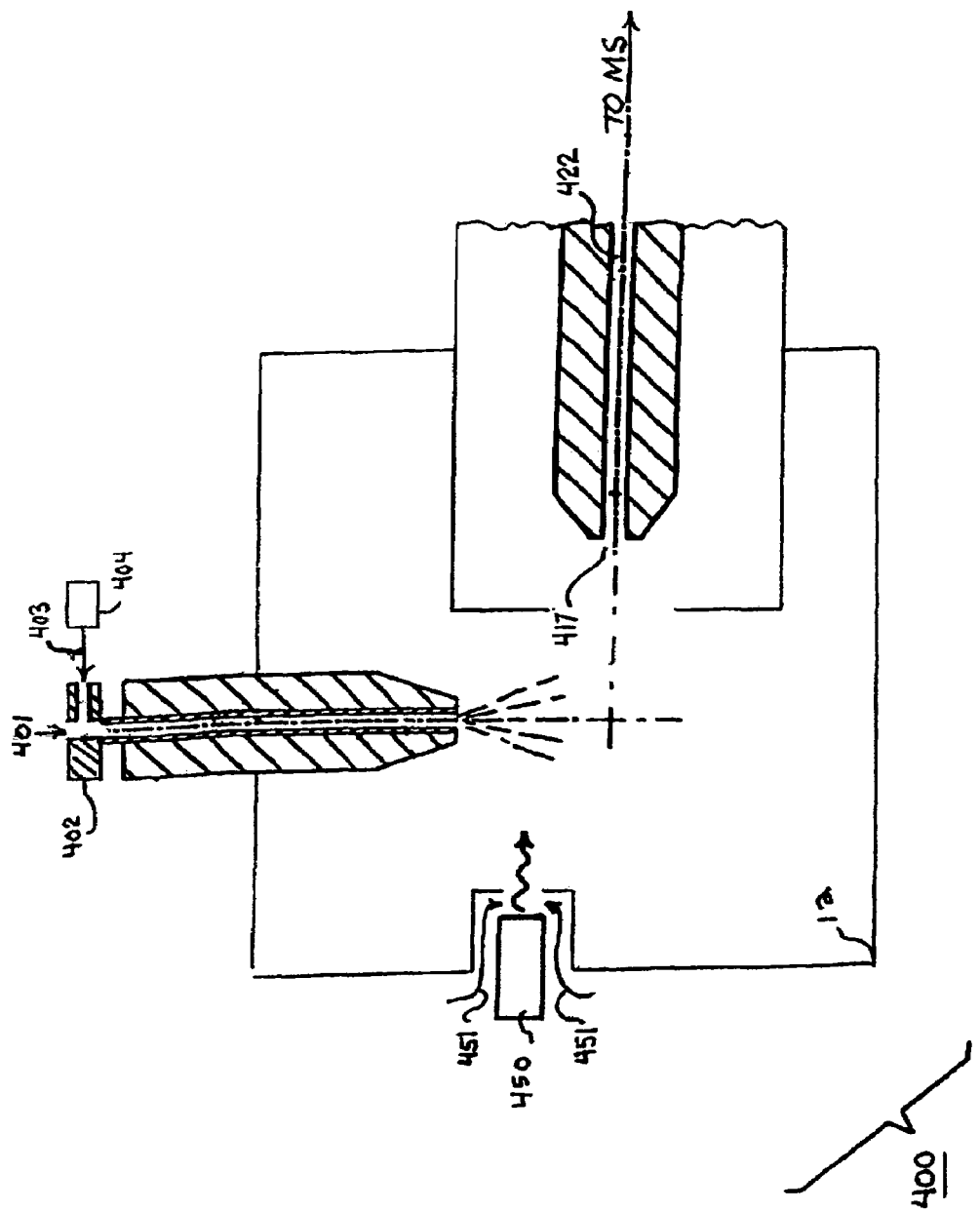
FIG. 8 is a diagram that illustrates an apparatus for employing the atmospheric pressure photoionization technique, according to still another embodiment of the present invention.

The present invention, according to another example embodiment thereof, may also employ dopants in order to help facilitate the ionization of an analyte. FIG. 8 illustrates an apparatus 400 configured according to one example embodiment of the present invention. In this embodiment, a nebulizer 402 is configured to receive via its inlet a liquid sample solution 401, and to also receive via another inlet a dopant 403 via a syringe pump 404. It is noted that this is merely one possible method of introducing dopant into the system, and that any conceivable method of doing so is contemplated by the present invention.

As previously mentioned, the apparatus may also comprise a drying gas source (not shown) which provides a stream of drying gas 451 across photon source 450 in order to prevent build-up on the photon source 450 that may result from exposure to contaminants such as the solvent, buffers, sample, etc., and that may cause a loss in UV transmission, a decline in ionization efficiency or noise. FIG. 8 illustrates one possible configuration of the drying gas stream, whereby the flow orientation of the stream of drying gas 451 is 360° degrees around the circumference of photon source 450 (thereby blowing radially across the lens toward its center and turning toward the ionization region). For this orientation of drying gas stream 451; it is preferable to maintain the flow velocity and volume low, so as to leave the flow in the ionization region relatively slow and stable. As previously explained, the stream of drying gas 451 may be maintained at a relatively high temperature in order to reduce the humidity and thus the likelihood of condensation on the lamp.

In operation, according to this embodiment of the present invention, a liquid sample solution 401, which is comprised of a solvent, the dopant and an analyte, is nebulized so as to form an aerosol, and the resultant aerosol droplets, which also comprise the solvent, the dopant and the analyte, proceed through the vaporizer. The aerosol is heated in order to promote vaporization of the aerosol. The vapor molecules exiting from the vaporized are subjected to photons generated by the photon source 450. The interaction of the photons from the photon source 450 with the vapor molecules causes ionization of the dopant molecules. Then, subsequent collisions between the ionized dopant and the analyte, either directly or indirectly, result in ionization of the analyte. (In some embodiments, a separate dopant is not used and the solvent performs the role as described here for the dopant) Once formed, the analyte ions are moved and directed by an electric field generating means towards and into the inlet orifice 417 of the second passageway 422.

In some embodiments, the motion of the analyte ions toward the inlet orifice of the second passageway may be assisted by gas flow. For example, an optional gas nozzle 652 is shown in FIG. 10. Gas is introduced through the nozzle and directed toward the ions such as to steer them toward the inlet orifice 617 of the second passageway 622. A typical gas nozzle 652 in this application could have an inner diameter of about 0.5 mm through which a stream of dry nitrogen, for example, is flowed at a rate of about 0.2 to about 1 l/min. Gas flow introduction can also be accomplished with other configurations, for example, an array of gas nozzles. In some embodiments using a gas flow means for moving ions toward the inlet orifice 617, the gas nozzle can also be an electrode, with a voltage applied to it such that an electric field is generated that also assists the motion of the ions into the inlet orifice. Thus the means for moving ions into the inlet orifice can comprise an electric field, or a gas flow, or a combination of an electric field and a gas flow. In the embodiments where the means comprises such a combination, the gas nozzle, for example, need not be an electrode, i.e., it need not participate in the electric field means. One feature of using gas flow to assist ion motion is that it can aid in desolvation of any residual droplets.

Figure 11:
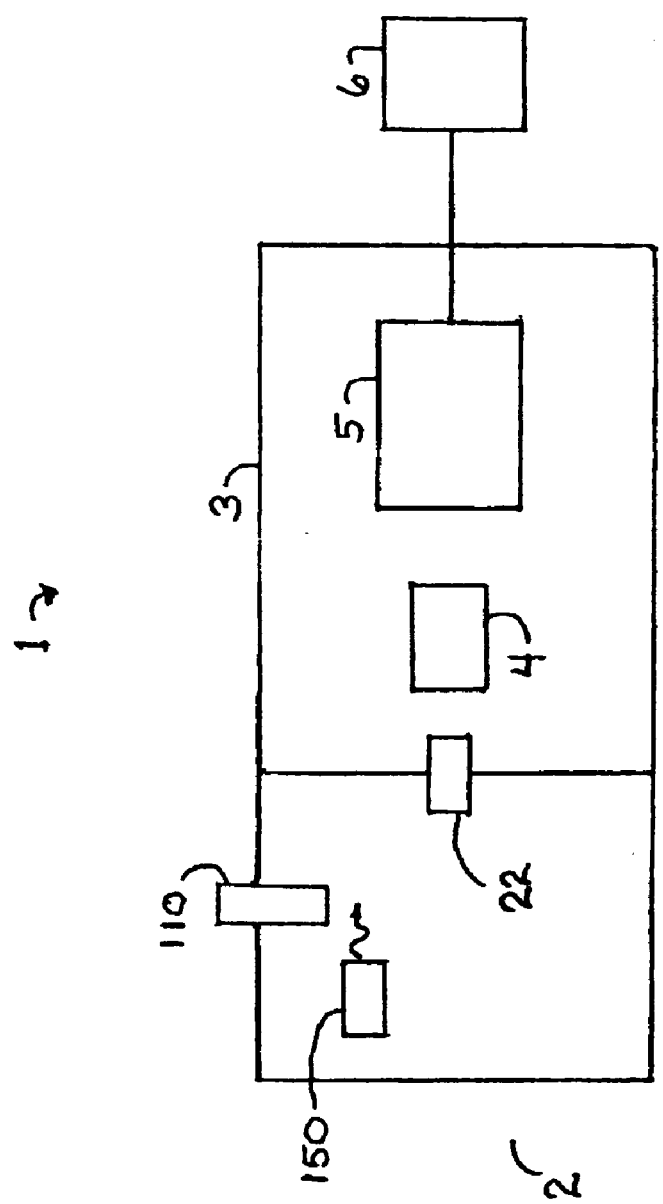
FIG. 11 is a diagram that illustrates a mass spectrometer system that incorporates an embodiment of the invention.

All embodiments of the invention can be used with a mass analyzer in a mass spectrometer system. For example, FIG. 11 illustrates such a mass spectrometer system 1. The atmospheric pressure ion source 2 comprises a vaporizer 110 and a passageway 22 in substantially orthogonal configuration. A photon source 150 forms ions by photoionization from vapor molecules exiting the vaporizer 110, and the ions are directed into the passageway 22 by a means not illustrated in the figure but as described above. Ions exit passageway 22 into a chamber 3 that may comprise one or more vacuum chambers. Ions are transported through an ion transport system 4 that may comprise ion optics such as ion guides and lenses, and then into a mass analyzer 4. Mass analyzer 4 includes an ion detector and may be any of the kinds of mass analyzers known in the art, e.g., quadrupole mass filter, time-of-flight, ion trap, ion cyclotron resonance (ICR) spectrometer, etc. If chamber 3 is at substantially atmospheric pressure, the mass analyzer can be an ion mobility mass spectrometer, for example. The ion detector in mass analyzer 1 is connected to a data acquisition or analysis system 6.

The present invention provides the capability of ionizing effluent from separation devices such as conventional high performance liquid chromatography or capillary electrophoresis at various flow rates. The invention further provides that analyte ions are separated from comparatively large volumes of vaporized aerosol from the column effluent, and then, while keeping out as much of the aerosol as possible, introducing the analyte ions into the vacuum system for mass detection and analysis. The invention provides the capability of separating analyte ions from the large volumes of vapor and directing the analyte ions from the ionization chamber (typically operating at atmospheric pressure) to the mass spectrometer (MS) (typically operating at $10^{-6}$ to $10^{-4}$ torr). The inventive separation capability preserves instrument sensitivity because the maximum amount of analyte ions is introduced into the vacuum system to be mass analyzed and detected. There is no reason other than convenience that the ion source needs to be at atmospheric pressure; the invention can be practiced with ion source pressures higher (e.g., about 2 atmospheres) or lower (a partial vacuum such as about 100 torr) than atmospheric. Specific pressures quoted are not intended to be limiting, and higher or lower pressures are considered to be within the scope of the invention. Similarly, the ion source can be flooded with particular gases such as nitrogen, or argon, or helium, etc., in some embodiments, for example to enhance photon transport or to aid in desolvation or ion formation by secondary processes.

With respect to the atmospheric pressure photoionization technique, substantially orthogonal ion sampling according to the present invention allows more efficient collection of the analyte by spraying the analyte ions past a sampling orifice, while directing the solvent vapor and solvated droplets in the aerosol away from the ion sampling orifice such that they do not enter the vacuum system.

With respect to the atmospheric pressure photoionization technique, the configuration described herein preserves instrument sensitivity because the maximum amount of analyte ions is introduced into the vacuum system to be mass analyzed and detected, but incomplete solvent-to-vapor phase change in the heater does not appear as noise, in contrast to the situation with the straight-on configurations of the prior art. Furthermore, the inventive sensitivity is preserved without overwhelming the vacuum system with large volumes of liquid droplets or vapor and residual liquid-phase solvent.

The noise level in an apparatus configured according to the present invention is reduced relative to current systems, resulting in increased signal relative to noise, and hence achieving greater sensitivity. Performance is simplified and the system is more robust because optimization of the position of the first passageway, gas flow and voltages show less sensitivity to small changes. The simplified performance and reduced need for optimization also result in a system less dependent upon flow rate and mobile phase conditions. The reduced need for optimization extends to changing mobile phase flow rates and proportions. Practically speaking, this means that an apparatus configured to employ the inventive system can be run under a variety of conditions without adjustment.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby and that its scope is to be determined by that of the appended claims.

What is claimed is:

1. A method for creating and transporting ions in an atmospheric pressure ion source, comprising:

photoionizing a stream of vaporized molecules directed approximately along a molecular axis using ultraviolet radiation;

guiding ions so created to a passageway having a central axis, the central axis and the molecular axis defining an angle in a range of about 20 to 180 degrees.

2. The method of claim 1, further comprising:

including a dopant reactive to ultraviolet radiation in the stream of vaporized molecules.

3. The method of claim 1, wherein the guiding comprises applying an electric field that directs ions to the passageway.

4. The method of claim 3, wherein the electric field is applied via an electrode.

5. The method of claim 4, wherein the electrode is situated in the passageway.

6. The method of claim 3, further comprising:

enclosing the passageway substantially such that an opening remains adjacent to the central axis to receive ions from the stream of vaporized molecules.

7. The method of claim 6, wherein the passageway is enclosed by a housing that comprises an electrode.

8. The method of claim 1, wherein the guiding comprises generating a flow of gas that forces ions to the passageway.

9. The method of claim 8, wherein the flow of gas is generated using a gas nozzle.

10. The method of claim 9, wherein the gas nozzle comprises an electrode.

* * * * *